(12) United States Patent
Narayanan et al.

(10) Patent No.: US 11,744,811 B2
(45) Date of Patent: *Sep. 5, 2023

(54) METHODS OF STABILIZING EPINEPHRINE

(71) Applicant: HIKMA PHARMACEUTICALS USA INC., Eatontown, NJ (US)

(72) Inventors: Eshwaran Narayanan, Chandler, AZ (US); Rajesh Wakaskar, Watertown, MA (US); Chandeshwari Chilampalli, Chandler, AZ (US); Thrimoorthy Potta, Phoenix, AZ (US); Venkat R. Goskonda, Phoenix, AZ (US)

(73) Assignee: Hikma Pharmaceuticals USA Inc., Eatontown, NJ (US)

( * ) Notice: Subject to any disclaimer, the term of this patent is extended or adjusted under 35 U.S.C. 154(b) by 239 days.

This patent is subject to a terminal disclaimer.

(21) Appl. No.: 17/363,146

(22) Filed: Jun. 30, 2021

(65) Prior Publication Data

US 2021/0338604 A1 Nov. 4, 2021

Related U.S. Application Data

(63) Continuation of application No. 16/242,101, filed on Jan. 8, 2019, now Pat. No. 11,077,075.

(60) Provisional application No. 62/615,491, filed on Jan. 10, 2018.

(51) Int. Cl.
*A61K 31/137* (2006.01)
*A61J 1/00* (2023.01)
*A61K 9/00* (2006.01)
*A61K 47/02* (2006.01)
*A61K 47/10* (2017.01)
*A61K 47/18* (2017.01)

(52) U.S. Cl.
CPC ............ *A61K 31/137* (2013.01); *A61J 1/00* (2013.01); *A61K 9/0043* (2013.01); *A61K 47/02* (2013.01); *A61K 47/10* (2013.01); *A61K 47/186* (2013.01)

(58) Field of Classification Search
CPC .... A61K 31/137; A61K 9/0043; A61K 47/01; A61K 47/10; A61K 47/186; A61J 1/00
See application file for complete search history.

(56) References Cited

U.S. PATENT DOCUMENTS

| | | | | |
|---|---|---|---|---|
| 5,534,242 | A | * 7/1996 | Henry | ............... A61K 31/165 514/622 |
| 2010/0174268 | A1 | 7/2010 | Wilmot et al. | |
| 2012/0083040 | A1 | 4/2012 | Krueger | |
| 2015/0374832 | A1 | 12/2015 | Surakitbanharn | |
| 2017/0216199 | A1 | 8/2017 | Potta et al. | |

OTHER PUBLICATIONS

International Preliminary Report on Patentability dated Jul. 14, 2020 in corresponding PCT application No. PCT/US2019/012602.

* cited by examiner

*Primary Examiner* — Trevor Love
(74) *Attorney, Agent, or Firm* — Wood, Phillips, Katz, Clark & Mortimer

(57) ABSTRACT

The present invention is directed to methods of stabilizing a pharmaceutical composition comprising epinephrine containing the steps filling a container, capping the container, assembling the container and placing the assembled capped container (assembled device) in a secondary packaging system.

19 Claims, No Drawings

METHODS OF STABILIZING EPINEPHRINE

BACKGROUND OF THE INVENTION

Epinephrine stimulates the alpha- and beta-adrenergic receptors of the sympathetic nervous system. Epinephrine binds to these adrenergic receptors leading to relief of many life-threatening symptoms of anaphylaxis including: relaxation of the smooth muscle in the bronchi of the lungs opening up the constricted airways; constriction of the blood vessels leading to decreased swelling of the tongue and throat and increased blood pressure; and finally, increased heart rate preventing or reversing cardiovascular collapse.

Currently, Epinephrine is commercially available as an injection (Adrenalin® a trademark of and available from Par Sterile Products, LLC) and an auto-injector (EpiPen® a trademark of and available from Mylan, Inc. and AuviQ® a trademark of and available from Sanofi Corporation). Epinephrine was previously available as a nasal spray (Adrenalin®) and an aerosol spray (Primatene® Mist trademark of Armstrong Pharmaceuticals, Inc.). The injection pens and the previous nasal spray have limited stability at room temperature.

The need to store many epinephrine products in a refrigerator is a major disadvantage for a pharmaceutical product. Accordingly, there is a need for developing a room temperature stable epinephrine product that addresses problems associated with the storage of a epinephrine at refrigerated conditions and patient convenience.

SUMMARY OF THE INVENTION

The present invention is directed to a method of stabilizing a pharmaceutical composition comprising:
from about 0.1% to about 12% w/w epinephrine base or a salt thereof; and
optionally, from about 50% to about 99% w/w water, from about 0.1% to about 2% w/w sodium chloride, from about 0.001 to about 0.02% w/w benzalkonium chloride ("BAC"), from about 0.1% to about 0.5% w/w sodium bisulfite, from about 0.01% to about 0.1% edetate disodium dihydrate and from about 20% to about 50% of 0.5 N hydrochloric acid ("HCl"), or
optionally, from about 10% to about 60% w/w ethanol, from about 11% to about 20% w/w water, from about 2% to about 20% w/w propylene glycol, from about 0.001% to about 0.02% w/w BAC, from about 0.01% to about 0.1% w/w edetate disodium dihydrate and from about 20% to about 50% w/w 0.5 N HCl,
comprising the steps of:
a. filling a container with the pharmaceutical composition under a vacuum or a gas overlay;
b. closing the container;
c. placing the closed container in a holder and actuator to create an assembled device;
d. placing the assembled device in a secondary packaging system under one or more conditions selected from the group consisting of with or without a gas overlay, with or without an oxygen absorbing means, and with or without oxygen indicator; and
e. sealing the secondary packaging system,
wherein the container is selected from the group consisting of a glass vial, plastic vial, glass bottle and a plastic bottle and the secondary packaging system is selected from the group consisting of a pouch and a blister package.

The present invention is further directed to a container comprising a pharmaceutical composition comprising:
from about 0.1% to about 12% w/w epinephrine base or a salt thereof; and
optionally, from about 50% to about 99% w/w water, from about 0.1% to about 2% w/w sodium chloride, from about 0.001 to about 0.02% w/w benzalkonium chloride ("BAC"), from about 0.1% to about 0.5% w/w sodium bisulfate, from about 0.01% to about 0.1% edetate disodium dihydrate and from about 20% to about 50% of 0.5 N hydrochloric acid ("HCl"), or
optionally, from about 10% to about 60% w/w ethanol, from about 11% to about 20% w/w water, from about 2% to about 10% w/w propylene glycol, from about 0.001% to about 0.02% w/w BAC, from about 0.01% to about 0.1% w/w edetate disodium dihydrate and from about 20% to about 50% w/w 0.5 N HCl.

DETAILED DESCRIPTION OF THE INVENTION

The present invention provides room temperature stable epinephrine compositions through novel packaging methods.

The epinephrine may be included in its free form or in the following forms: a salt; an acid addition salt of an ester; an amide; an enantiomer; an isomer; a tautomer; a prodrug; a derivative of an active agent of the present invention; different isomeric forms, including, but not limited to enantiomers and diastereoisomers, both in pure form and in admixture, including racemic mixtures; and enols. The term "epinephrine" is also meant to encompass derivatives that are produced from another compound of similar structure by the replacement of one atom, molecule or group by another.

As used herein, all numerical values relating to amounts, weights, and the like, that are defined as "about" each particular value is plus or minus 10%. For example, the phrase "about 10% w/w" is to be understood as "9% w/w to 11% w/w." Therefore, amounts within 10% of the claimed value are encompassed by the scope of the claims.

All weights herein refer to % w/w or percent weight of the total composition.

The present invention is directed to a method of stabilizing a pharmaceutical composition comprising:
from about 0.1% to about 12% w/w epinephrine base or a salt thereof; and
optionally, from about 50% to about 99% w/w water, from about 0.1% to about 2% w/w sodium chloride, from about 0.001 to about 0.02% w/w benzalkonium chloride ("BAC"), from about 0.1% to about 0.5% w/w sodium bisulfite, from about 0.01% to about 0.1% edetate disodium dihydrate and from about 20% to about 50% of 0.5 N hydrochloric acid ("HCl"), or
optionally, from about 10% to about 60% w/w ethanol, from about 11% to about 20% w/w water, from about 2% to about 20% w/w propylene glycol, from about 0.001% to about 0.02% w/w BAC, from about 0.01% to about 0.1% w/w edetate disodium dihydrate and from about 20% to about 50% w/w 0.5 N HCl,
comprising the steps of:
a. filling a container with the pharmaceutical composition under a vacuum or a gas overlay;
b. closing the container;
c. placing the closed container in a holder and actuator to create an assembled device;
d. placing the assembled device in a secondary packaging system under one or more conditions selected from the group consisting of with or without a gas overlay, with or without an oxygen absorbing means, and with or without oxygen indicator; and e. sealing the secondary packaging system, wherein the container is selected from the group consisting of a glass vial, a plastic vial, a glass bottle and a plastic bottle and the secondary packaging system is selected from the group consisting of a pouch and a blister package.

The present invention is further directed to a container comprising a pharmaceutical composition comprising:

from about 0.1% to about 12% w/w epinephrine base or a salt thereof; and optionally, from about 50% to about 99% w/w water, from about 0.1% to about 2% w/w sodium chloride, from about 0.001 to about 0.02% w/w benzalkonium chloride ("BAC"), from about 0.1% to about 0.5% w/w sodium bisulfate, from about 0.01% to about 0.1% edetate disodium dihydrate and from about 20% to about 50% of 0.5 N hydrochloric acid ("HCl"), or optionally, from about 10% to about 60% w/w ethanol, from about 11% to about 20% w/w water, from about 2% to about 10% w/w propylene glycol, from about 0.001% to about 0.02% w/w BAC, from about 0.01% to about 0.1% w/w edetate disodium dihydrate and from about 20% to about 50% w/w 0.5 N HCl.

In a preferred embodiment, the gas used in the methods of the present invention is nitrogen or an inert gas. As used herein, the term "inert gas" refers to the gaseous form of an element in which the atoms have a full valence shell. More preferably the inert gas used in the methods of the present invention is selected from the group consisting of helium, neon, argon, krypton, xenon and radon.

In another preferred embodiment, the assembled device is an intranasal device. In a more preferred embodiment, the assembled device is an intranasal device comprising a glass vial, a rubber stopper, a vial holder and an actuator.

In another preferred embodiment, the secondary packaging system contains an oxygen absorbing means. Preferably, the oxygen absorbing means is provided by one or more walls of the secondary packaging system or by an auxiliary oxygen absorber placed between two or more walls of the secondary packaging system. In another preferred embodiment, the oxygen absorbing means is selected from the group consisting of a pellet, a strip, a sheet and a packet.

In a preferred embodiment, the auxiliary oxygen absorber is an iron based or polymer based oxygen absorber. In a more preferred embodiment, the auxiliary oxygen absorber is an iron based oxygen absorber. In an even more preferred embodiment, the iron based auxiliary oxygen absorber provides absorption of from about 1 to about 3,000 cubic centimeters of oxygen, yet more preferably from about 10 to about 1,000 cubic centimeters of oxygen, even more preferably from about 50 to about 500 cubic centimeters of oxygen and most preferably about 100 cubic centimeters of oxygen.

In another preferred embodiment, the secondary packaging system contains an oxygen indicator. In another preferred embodiment, the oxygen indicator means is selected from the group consisting of a pellet, a strip, a sheet and a packet.

The disclosed embodiments are simply exemplary embodiments of the inventive concepts disclosed herein and should not be considered as limiting, unless the claims expressly state otherwise.

The following examples are intended to illustrate the present invention and to teach one of ordinary skill in the art how to use the compositions of the invention. They are not intended to be limiting in any way.

EXAMPLES

Preferred compositions of the present invention are described in Tables 1 and 2, below.

TABLE 1

Composition 1

| Ingredients | % w/w | Function |
|---|---|---|
| Epinephrine Base | 2.962 | Active Ingredient |
| Benzalkonium Chloride | 0.010 | Preservative |
| Sodium Chloride | 0.600 | Tonicity Agent |
| Sodium Bisulfite | 0.150 | Anti-Oxidant |
| Edetate Disodium Dihydrate (EDTA) | 0.050 | Chelating agent |
| Hydrochloric acid (0.5N) | 32.930 | pH modifier |
| Purified Water | 63.298 | Vehicle |
| Solution containing 2.0N NaOH and 0.5N HCl | Adjust to pH 4.5 ± 0.1 | pH adjustment |

TABLE 2

Composition 2

| Ingredients | % w/w | Function |
|---|---|---|
| Epinephrine Base | 3.178 | Active Ingredient |
| Benzalkonium Chloride | 0.010 | Preservative |
| Dehydrated Alcohol (Ethanol) | 40.000 | Co-Solvent |
| Propylene Glycol | 5.000 | Co-Solvent |
| Sodium Bisulfite | 0.150 | Anti-Oxidant |
| Edetate Disodium Dihydrate | 0.050 | Chelating agent |
| Hydrochloric acid (0.5N) | 35.471 | pH modifier |
| Purified Water | 16.141 | Vehicle |
| Solution containing 2.0N NaOH and 0.5N HCl | Adjust pH to 4.5 ± 0.1 | pH adjustment |

Example 1. Preparation of a Composition of the Present Invention

All the solvents were degassed and purged with nitrogen prior to use. All the excipients including propylene glycol, ethanol, 0.5 N hydrochloric acid, edetate disodium dihydrate, sodium bisulfite and benzalkonium chloride were then dissolved in water while stirring at room temperature. Epinephrine base was then added to the excipient solution. Finally, sodium hydroxide/hydrochloric acid was used to adjust final pH to 4.5±0.1 to create the compositions in Tables 1 and 2, above.

Example 2. Nasal Spray Device Filling Procedure

A composition of the present invention is filled into unit dose nasal spray device vials under vacuum or a gas atmosphere such as nitrogen. Thereafter a rubber stopper is inserted and a vial holder and actuator attached. These unit dose nasal spray devices are then packaged in a secondary packaging material.

Example 3. Packaging Procedure

The Epinephrine nasal spray devices are packaged in a secondary packaging system (e.g. a pouch, blister or any other enclosed package) under a gas overlay. There are several ways in which the skilled in the art may practice the packaging step. The description below refers to only some embodiments of the invention and is not limiting in any way.

The secondary packaging system may be comprised of oxygen absorbers or may hold an oxygen absorber. The gas overlay may be provided by a tank placed externally to the packaging. The gas is transferred from the tank to the packaging via a hose, tube or other means at a pressure above 0.01 pounds per square inch ("p.s.i."), preferably from about 0.1 to about 5 p.s.i.

If an oxygen absorber is introduced into the packaging system, then the oxygen absorber is placed into the secondary packaging under a gas overlay. The secondary packaging system may also hold an oxygen indicator.

If an oxygen absorber and or oxygen indicator are held in the secondary packaging, then the presence of the oxygen absorber and or oxygen indicator may be assured by visual inspection or an external sensor.

Example 4. Stability Testing

The formulations listed in Table 1 and 2 were filled into unit dose nasal spray device vials under vacuum or a gas overlay such as nitrogen. Thereafter a rubber stopper is inserted and a vial holder and actuator attached. The assembled devices were packaged in a secondary packaging system (e.g. a pouch, blister or any other enclosed package) under a gas overlay, vacuum or normal atmospheric conditions with the appropriate placement of an oxygen absorber in the pouch. These units were then subjected to stability testing at 55° C.±2° C., 40° C.±2° C./75%±5% RH and 25° C.±2° C./60%±5% RH.

The stability data was collected at zero time point, 3 months and 6 months at 25° C. as well as zero-time point, 2 months, 3 months and 6 months at 40° C. for the hydro-alcoholic formulation. Furthermore, for the aqueous formulation, the stability data was collected at zero time point, 3 months and 6 months at 25° C. as well as zero time point, 2 months and 6 months at 40° C. Assay and impurities were detected using high performance liquid chromatography with an ultraviolet detector. The assay was performed at 280 nm and is indicated as a % of initial concentration. For all impurities, analysis was performed at 210 nm and 280 nm and expressed as a % area. Amounts of individual impurities are listed in Tables 3 to 6 as a percentage of the area of each formulation along with amount of total impurities. "BQL" refers to "Below Quantifiable Limit" and "ND" refers to "Not Detected." The BQL designation is used to describe those peaks that are less than 0.05%.

TABLE 3

Stability Data for Pouched Epinephrine Nasal Spray Formulation of Table 2 stored at 25° C. ± 2° C./60% ± 5% relative humidity with oxygen absorbers (25° C.)

|  | RRT | T = 0 | 3M | 6M |
|---|---|---|---|---|
| Assay |  | 101.32 | 92.83 | 101.79 |
| Appearance |  | Clear, colorless | Clear, colorless | Clear, colorless |
| Imp-F | 0.19 | 0.16 | 1.08 | 2.32 |
| Epinephrone | 1.34 | ND | BQL | BQL |
| Methoxy | 1.77 | 0.07 | 0.05 | 0.06 |
| Unknown | 0.21 | ND | 0.03 | 0.07 |
| Impurities | 0.23 | ND | ND | BQL |
| (%) | 1.20 | ND | ND | BQL |
|  | 2.45 | ND | ND | BQL |
| Total Impurities (%) |  | 0.23 | 1.16 | 2.45 |

TABLE 4

Stability Data for Pouched Epinephrine Nasal Spray Formulation of Table 2 stored at 40° C. ± 2° C./75% ± 5% relative humidity with oxygen absorbers (40° C.)

|  | RRT | T = 0 | 2M | 3M | 6M |
|---|---|---|---|---|---|
| Assay |  | 101.32 | 83.12 | 91.78 | 100.20 |
| Appearance |  | Clear, colorless | Clear, colorless | Clear, colorless | Clear, colorless |
| Imp-F | 0.19 | 0.16 | 4.56 | 6.40 | 7.56 |
| Epinephrone | 1.34 | ND | BQL | BQL | BQL |
| Methoxy | 1.77 | 0.07 | 0.06 | 0.05 | 0.05 |
| Unknown | 0.20 | ND | ND | ND | 0.13 |
| Impurities | 0.21 | ND | 0.26 | 0.05 | 0.08 |
| (%) | 0.26 | ND | 0.13 | 0.12 | 0.30 |
|  | 1.19 | ND | 0.06 | BQL | BQL |
|  | 1.71 | ND | BQL | BQL | 0.05 |
|  | 1.95 | ND | ND | ND | 0.07 |
|  | 2.45 | ND | 0.06 | 0.05 | 0.73 |
|  | 2.92 | ND | ND | ND | 0.19 |
|  | 2.95 | ND | ND | ND | 0.13 |
|  | 2.97 | ND | ND | ND | 0.16 |
| Total Impurities (%) |  | 0.23 | 5.13 | 6.67 | 9.45 |

TABLE 5

Stability Data for Pouched Epinephrine Nasal Spray Formulation of Table 1 stored at 25° C. ± 2° C./60% ± 5% relative humidity with oxygen absorbers (25° C.)

|  | RRT | T = 0 | 3M | 6M |
|---|---|---|---|---|
| Assay |  | 101.32 | 103.80 | 104.79 |
| Appearance |  | Clear, colorless | Clear, colorless | Clear, colorless |
| Imp-F | 0.19 | 0.16 | 1.54 | 4.00 |
| Epinephrone | 1.34 | ND | BQL | BQL |
| Methoxy | 1.77 | 0.07 | 0.06 | 0.05 |
| Unknown | 0.21 | ND | BQL | BQL |
| Impurities | 0.72 | ND | BQL | BQL |
| (%) | 0.83 | ND | BQL | ND |
|  | 3.09 | ND | BQL | 0.05 |
| Total impurities (%) |  | 0.23 | 1.60 | 4.10 |

TABLE 6

Stability Data for Pouched Epinephrine Nasal Spray Formulation of Table 1 stored at 40° C. ± 2° C./75% ± 5% relative humidity with oxygen absorbers (40° C.)

|  | RRT | T = 0 | 2M | 6M |
|---|---|---|---|---|
| Assay |  | 101.32 | 91.40 | 103.10 |
| Appearance |  | Clear, colorless | Clear, colorless | Clear, colorless |
| Imp-F | 0.19 | 0.16 | 6.81 | 6.90 |
| Epinephrone | 1.34 | ND | BQL | BQL |
| Methoxy | 1.77 | 0.07 | 0.06 | 0.05 |
| Unknown | 0.21 | ND | 0.09 | 0.07 |
| Impurities | 0.70 | ND | BQL | ND |
| (%) | 1.71 | ND | ND | 0.07 |
|  | 1.92 | ND | ND | 0.07 |
|  | 1.95 | ND | ND | 0.05 |
|  | 2.00 | ND | ND | 0.05 |
|  | 2.09 | ND | ND | 0.06 |
|  | 2.27 | ND | ND | 0.05 |

TABLE 6-continued

Stability Data for Pouched Epinephrine Nasal Spray Formulation of Table 1 stored at 40° C. ± 2° C./75% ± 5% relative humidity with oxygen absorbers (40° C.)

| RRT | T = 0 | 2M | 6M |
|---|---|---|---|
| 2.41 | ND | ND | 0.08 |
| 2.84 | ND | ND | 0.19 |
| 2.90 | ND | ND | 0.29 |
| 2.93 | ND | ND | 0.31 |
| 2.98 | ND | ND | 0.25 |
| Total Impurities (%) | 0.23 | 6.96 | 8.49 |

Compositions exhibit less than 20% of total impurities at 25° C. 60% RH±5% RH and 40° C. 75% RH±5% RH after 6 months. See, Tables 3-6.

Further, it is known Epinephrine is highly susceptible to oxidative degradation in solutions. Various anti-oxidants were used to stabilize Epinephrine in formulations during accelerated and long-term stability studies. Among the tested anti-oxidants and stabilizers, sodium bisulfite, in combination with edetate disodium dihydrate, was promising. Sodium bisulfite was used in the above listed formulations as an antioxidant at a concentration of 0.15% w/w to stabilize the formulations. Edetate disodium dihydrate was used as stabilizer at 0.05% w/w. However, sulfite and bisulfite ions are known to react with the optically active side chain of epinephrine, in turn forming Epinephrine Sulfonic acid, also known as impurity F. Temperature plays a significant role in the formation of impurity F, as is evident from the stability data. Most of the marketed products use either sodium bisulfite or sodium metabisulfite as anti-oxidants at higher concentrations to stabilize epinephrine formulations and as a result high amounts of impurity F were seen in those formulations towards the end of their shelf life.

For the hydro-alcoholic formulations, 2.32% and 7.56% of impurity F was observed after a period of 6 months at 25° C./60% RH±5% RH, and 40° C./75% RH±5% RH, respectively. In the case of aqueous formulation, 4.00% and 6.90% of impurity F was observed after a period of 6 months at 25° C./60% RH±5% RH and 40° 0 C/75% RH±5% RH, respectively. The lower percentage of impurity F formation in the case of hydro alcoholic formulations may be attributed to the change in solvent system. All other impurities were within acceptable limits and both the aqueous and hydro-alcoholic formulations were clear and colorless during stability studies. In conclusion, the use of said packaging technique significantly improved the stability of Epinephrine formulations.

What is claimed is:

1. A device comprising a container, wherein the container comprises a pharmaceutical composition comprising from about 1% to about 12% w/w epinephrine, from about 10% to about 60% w/w ethanol, from about 2% to about 20% w/w propylene glycol, from about 0.001% to about 0.02% w/w benzalkonium chloride and from about 0.01% to about 0.1% w/w edetate disodium dihydrate, wherein w/w denotes weight by total weight of the composition and wherein the composition comprises epinephrine as the only active ingredient.

2. The device of claim 1, wherein the device is an intranasal device.

3. The device of claim 1, wherein the container is selected from the group consisting of a glass vial, a plastic vial, a glass bottle and a plastic bottle.

4. The device of claim 1, wherein the container is a glass vial.

5. The device of claim 1, wherein the container is a unit dose vail.

6. The device of claim 1, wherein the container is stoppered with a rubber stopper.

7. The device of claim 1, further comprising a vial holder and an actuator.

8. The device of claim 1, further comprising a rubber stopper, a vial holder and an actuator, wherein the container is a glass vial.

9. The device of claim 1, wherein the container further comprises a gas layer.

10. The device of claim 9, wherein the gas layer consists of a gas selected from the group consisting of helium, neon, argon, krypton, xenon, radon and nitrogen.

11. The device of claim 9, wherein the gas layer consists of nitrogen.

12. A secondary packaging system comprising the device of claim 1 and an oxygen absorbing means.

13. The secondary packaging system of claim 12, wherein the secondary packaging system is a pouch or a blister package.

14. The secondary packaging system of claim 12, wherein the oxygen absorbing means is provided by one or more walls of the secondary packaging system.

15. The secondary packaging system of claim 12, wherein the oxygen absorbing means is an auxiliary oxygen absorber placed between two or more walls of the secondary packaging system.

16. The secondary packaging system of claim 12, wherein the oxygen absorbing means is an iron based oxygen absorber.

17. The secondary packaging system of claim 16, wherein the iron based oxygen absorber is in a form of a pellet, a strip, a sheet or a packet.

18. The secondary packaging system of claim 12, further comprising an oxygen indicator.

19. The secondary packaging system of claim 18, wherein the oxygen indicator is in a form of a pellet, a strip, a sheet or a packet.

* * * * *